United States Patent [19]

Changaris

[11] Patent Number: 5,282,842
[45] Date of Patent: Feb. 1, 1994

[54] METHOD OF INDUCING TANNING BY PULSED LIGHT AND APPARATUS TO EFFECT SAME

[76] Inventor: David G. Changaris, 1132 Rostrevor Cir., Louisville, Ky. 40205

[21] Appl. No.: 675,689

[22] Filed: Mar. 27, 1991

[51] Int. Cl.$^5$ .............................................. A61N 5/06
[52] U.S. Cl. ..................................... 607/88; 607/90; 607/91; 607/94; 607/81
[58] Field of Search ............... 128/362, 371, 372, 376, 128/395, 396, 397; 606/3, 9; 250/497.1, 498.1, 503.1, 504 R; 607/77, 81, 84, 88, 90, 91, 94

[56] References Cited

U.S. PATENT DOCUMENTS

| | | | |
|---|---|---|---|
| 3,042,046 | 7/1962 | Willems | 128/395 |
| 3,773,049 | 11/1973 | Rabichev et al. | 128/362 |
| 4,309,616 | 1/1982 | Wolff | 250/504 R |
| 4,469,102 | 9/1984 | Fish | 273/371 |
| 4,558,700 | 12/1985 | Mutzhas | 128/395 |
| 4,674,507 | 6/1987 | Basso | 128/395 |
| 4,712,014 | 12/1987 | Eich | 128/396 |
| 4,874,361 | 10/1989 | Obagi | 128/395 |

FOREIGN PATENT DOCUMENTS 1435262  11/1988  U.S.S.R. .......................... 250/504 R

OTHER PUBLICATIONS

Changaris, Jul. 1991, unpub., "The Tanning Book", pp. 5, 10 & 11.
*DNA Photoreactivating Enzyme from Human Tissues*: Ogut, D'Ambrosio, Samuel, and Sutherland; pp. 47-56.
*Isolation and Characterization of a Marsupial DNA Photolayse*; Sabourin and Ley; "Photochemistry and Photobiology"; vol. 47, No. 5, pp. 719-723 (1988).
*Pyrimidine Dimer Formation and Repair in Human Skin*; Sutherland, Harber, and Kochevar; "Cancer Research"; vol. 40, pp. 3181-3185 (Sep. 1980).
*Excision Repair of UVR-Induced Pyrimidine Dimers in Corneal DNA*; Freeman, Applegate, and Ley; "Photochemistry and Photobiology"; vol. 47, No. 1, pp. 159-163 (1988).
*Execision Repair of Pyrimidine Dimers in Marsupial Cells*; Applegate and Ley, "Photochemistry and Photobiology"; vol. 45, No. 2, pp. 241-245 (1987).
*DNA Photolyases: Physical Properties, Action Mechanism, and Roles in Dark Repair*; Sancar; "Mutation Research, DNA Repair"; vol. 236, pp. 147-160 (1990).
*A Role for Sunlight in Skin Cancer: UV-Induced p 53 Mutations in Squamous Cell Carcinoma*; Brash, Rudolph, Simon, Lin, McKenna, Baden, Halperin, and Ponten; "Proceedings National Academy of Science"; vol. 88, pp. 10124-10128 (Nov. 1991).
*Purification of Escherichia coli DNA Photolyase*; Sancar, Smith, and Sancar; "The Journal of Biological Chemistry"; vol. 259, No. 9, pp. 6028-6032 (May 10, 1984).
*Sequences of the Escherichia coli Photolyase Gene and Protein*; Sancar, Smith, Lorence, Rupert, and Sancar; "The Journal of Biological Chemistry"; vol. 259, No. 9, pp. 6033-6038 (May 10, 1984).
*Biochemical Hetrogenity in Xeroderma Pigmentosum Complementation Group E*; Keeney, Wein, and Linn; "Mutation Research, DNA Repair"; vol. 273, pp. 49-56 (1992).
*Defective DNA Endonuclease Activities in Fanconi's Anemia Cells, Complementary Groups A and B*; Lambert, Tsongalis, Lambert, Hang, and Parrish; "Mutation Research, DNA Repair"; vol. 273, pp. 57-71 (1992).
*Workshop on DNA Repair*; Lehmann, Hoeijmakers, van (List continued on next page.)

Primary Examiner—Jessica J. Harrison
Attorney, Agent, or Firm—Middleton & Reutlinger

[57] ABSTRACT

A method and apparatus to effect tanning in humans. The method utilizes very short discrete pulses, with a dark period of low to zero energization between discrete pulses, of ultraviolet or visible light irradiation of selected wave length to effect the tanning. Different apparati are disclosed to carry out the invention. One type of apparatus continuously generates irradiation of the selected wave length and projects that irradiation through mechanical pathblockers to create the discrete pulses. Another type of apparatus intermittently generates irradiation in the desired discrete pulse and of the desired wave length to create the desired effect.

41 Claims, 6 Drawing Sheets

OTHER PUBLICATIONS

Zeeland, Backendorf, Bridges, Collins, Fuchs, Margison, Montesano, Moustacchi, Natarajan, Radman, Sarasin, Seeberg, Smith, Stefanini, Thompson, van der Schans, Weber, and Zdzienicka; "Mutation Research, DNA Repair"; vol. 273, pp. 1-28 (1992).

*A Rapid DEAE Disk Assay for photoreactivation of Pyrimidine Dimers in [$^3H$]DNA*; Farland and Sutherland; "Analytical Biochemistry", vol. 97, pp. 376-381 (1979).
*Analysis of Photoenzymatic Repair of UV Lesions in DNA by Single Light Flishes*; Nishioka and Harm; "Mutation Research"; vol. 16, pp. 121-131 (1972).

METHOD OF INDUCING TANNING BY PULSED LIGHT AND APPARATUS TO EFFECT SAME

BACKGROUND OF THE INVENTION

This invention relates to a new technique to induce "tanning" in humans, by utilizing very short, discrete pulses of ultraviolet ("UV") and/or visible light energy of selected wave length, for example about 250-400 nanometers ("nm"), preferably about 280-300 nm with an optimum of about 290 nm.

The prior art discloses several apparati to induce artificial tanning of human skin. See, U.S. Pat. No. 4,862,886 (Clarke); U.S. Pat. No. 4,794,925 (Kei Mori); U.S. Pat. No. 4,711,448 (Tsvi Goldenberg); U.S. Pat. No. 4,611,327 (Clarke;) and U.S. Pat. No. 4,469,102 (Fish). The prior art devices generally utilize a source of continuous fluorescent ultraviolet radiant energy, usually within the Ultraviolet A ("UVA") spectrum (wave length 320 to 390 nm), with very limited amounts of Ultraviolet B ("UVB") spectrum (wave length, 286 to 320 mm); the Ultraviolet C spectrum ("UVC", wave length 40-286 nm) is seldom utilized in tanning machines.

Tanning occurs largely through a process known as melanogenesis, a process which turns skin darker by stimulating the melanin-containing cells known as melanocytes to generate small packets of pigment. When an individual increases the pigment in his or her skin the emotional result is generally a sense of well-being and perceived improved appearance. UVB light is a known initiator for melanogenesis with a peak "tanning efficiency" at a wave length of about 290 nm. However, UVB has heretofore been saddled with safety concerns. This is because, even though it is known that peak tanning efficiency occurs at about 290 nm, it is also true that exposure to UVB energy has a significant risk of the toxic result of erythema, or "sun burn". Because of this risk, Federal Regulations (e.g., 21 CFR §1040.20(ii)(c)(1)), place strict limitations on the amount of UVB radiation a recipient may be exposed to (usually, the total energy source must emit less than 0.3% UVB). Consequently, prior art tanning devices are ordinarily required to utilize UVA energy sources (e.g., a continuously emitting fluorescent light tube). As a result, currently available tanning booths and the like are required to use the least efficient source of radiant energy to promote tanning.

Light above but near 320 nm is within the UVA spectrum. UVA will induce the so called "immediate tanning" related to the oxidation of pre-existing melanin, the dark pigment within skin. It is thought that this stimulus of tanning is most likely dependent upon the minimal but still present UVB within commercially available tanning light sources. These currently available suntanning light sources use continuous light sources that produce a series of potentially toxic results, for example the rapid destruction of genetic (thymine dimer formation) and protein structure through the build up of cellular toxins, presumably superoxides and resulting products. Such toxic effects are often divided into both short and long term events. The short term events include sun burn, corneal clouding, and retinal damage. The long term effects include premature aging of the skin and accelerated cancer incidence (e.g., melanoma).

SUMMARY OF THE INVENTION

I have discovered that the tanning can occur with pulsed irradiation, and that it is not necessary to have a continuous source of UV energy to induce tanning. Surprisingly, by subjecting the skin to very short, discrete pulses of energy, it is possible to effect an inducement of the melanocytes to produce pigmentation changes equivalent to those produced by continuous UV irradiation sources, but without manifesting tissue injury (e.g., sunburn) that is so often associated with those prior art devices. Thus, the present invention emits short discrete pulses of energy which will permit tanning but with significantly reduced injury to structural elements such as collagen and cells.

The exposure to pulsed light will induce tanning depending upon the wave lengths defined. Pulses on the order of picoseconds to milliseconds produce an irradiation cycle which will prevent buildup toxic products known to accumulate during continuous exposure to UV energy. An important feature of the present invention is that pulsed energy also allows sufficient time between energy impingements for the resident enzymes within the irradiated area to eliminate light-induced toxic products, for example, superoxides, thymine dimers, oxidized light-sensitive proteins (i.e., the characteristic byproducts of skin burning). Thus, the total accumulated exposure to the energy source and the absolute time required to achieve the desired tanning level is markedly reduced.

Exposure to continuous light damages DNA, by altering the thymine structure to produce thymine dimers; the rate of thymine dimer formation is thought to be critical to the integrity of skin. It is also known than continuous ultraviolet exposure causes thymine bases to become thymine dimers. Many have speculated that this in turn contributes to premature aging and increasing incidence of skin cancer.

The body's response to correct the formation of thymine dimers includes a process known as photoreactivation to produce an enzyme known as photolyase, and another process known as dark repair. The majority of thymine dimer repair is believed to occur through photolyase. The energy absorption characteristics of UV irradiation to produce or inhibit UV-induced skin damage are generally known. Photolyase production is driven most efficiently by blue to green visible light (wave length, 375-500 nm); dark repair occurs without light. In conducting experiments to test my invention as described herein, I have come to believe and understand that photoreactivation or photolyase can be induced or initiated with discrete pulses of ultraviolet energy in the high end of the UVA range (wave length, above 375 nm), even by a single discrete pulse. Ordinarily, continuous exposure to UV light leads to the accumulation of toxic by-products such as superoxides, which can and do degrade the photoreactive systems thought to be present in human photolyase. However, it appears that serial exposure to discrete pulses of UV energy in this range will not produce the usual toxic byproducts associated with continuous UV exposure provided by present tanning booths, but will in fact enhance the repair of thymine dimers. This is thought to be because, with a discrete pulse, there is a "dark" portion between the active portion of the energized pulse. Because there is a dark non-energized portion of each discrete pulse, the cumulative energy within each pulse is sufficient to induce photolyase, but not sufficient to induce or create the toxic by-products.

A device according to the present invention is provided whereby the cumulative energy input is limited to an amount which will be sufficient to stimulate the melanocytes within the skin to induce melanogenesis, but which will be insufficient to produce the toxic products known to be associated with excess exposure of the skin to UV irradiation.

Because the accumulation of toxic products usually associated with exposure to continuous sources of light-source energy is so vastly reduced when utilizing discrete pulses of energy, with the present invention it will be possible to utilize the more efficient UVB energy source within its most efficient tanning range (for example, about 290 nm), without the heretofore feared toxic side effects.

Accordingly, it is an object of the present invention to provide a method and apparati to promote suntanning in humans resulting from exposure to very short, discrete pulses of energy of selected wave length to promote suntanning, without consequent risk of sunburn or other toxic results.

It is a further object of the present invention to provide an apparatus equipped with a light energy source to provide very short discrete pulses of energy of multiple selected wave lengths to permit suntanning.

It is a further object of the present invention to provide a method and apparati to promote suntanning in a very short elapsed time.

Further objects of the present invention will become obvious to those skilled in the art, by reference to the following specification, drawings and claims.

DESCRIPTION OF PREFERRED EMBODIMENTS

Figure 4:
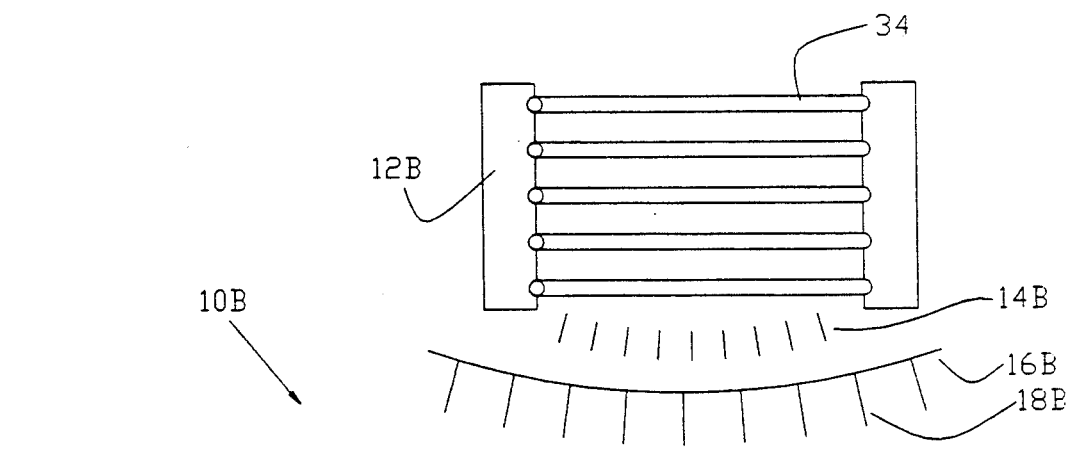
FIGS. 4 and 5 depict alternate embodiments to mechanically produce discrete pulses of light energy of selected wave length.
Figure 4:
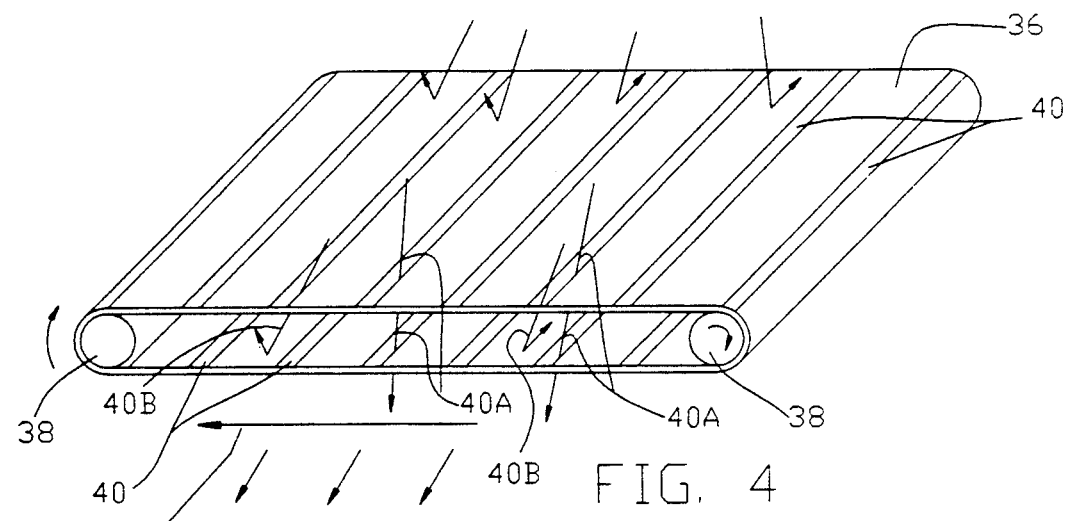
Figure 5:
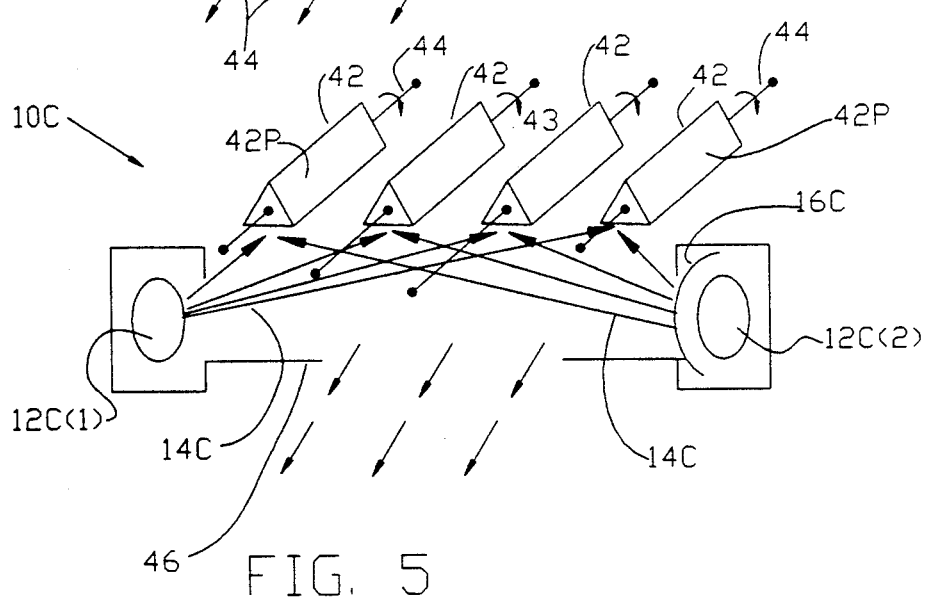
Figure 6:
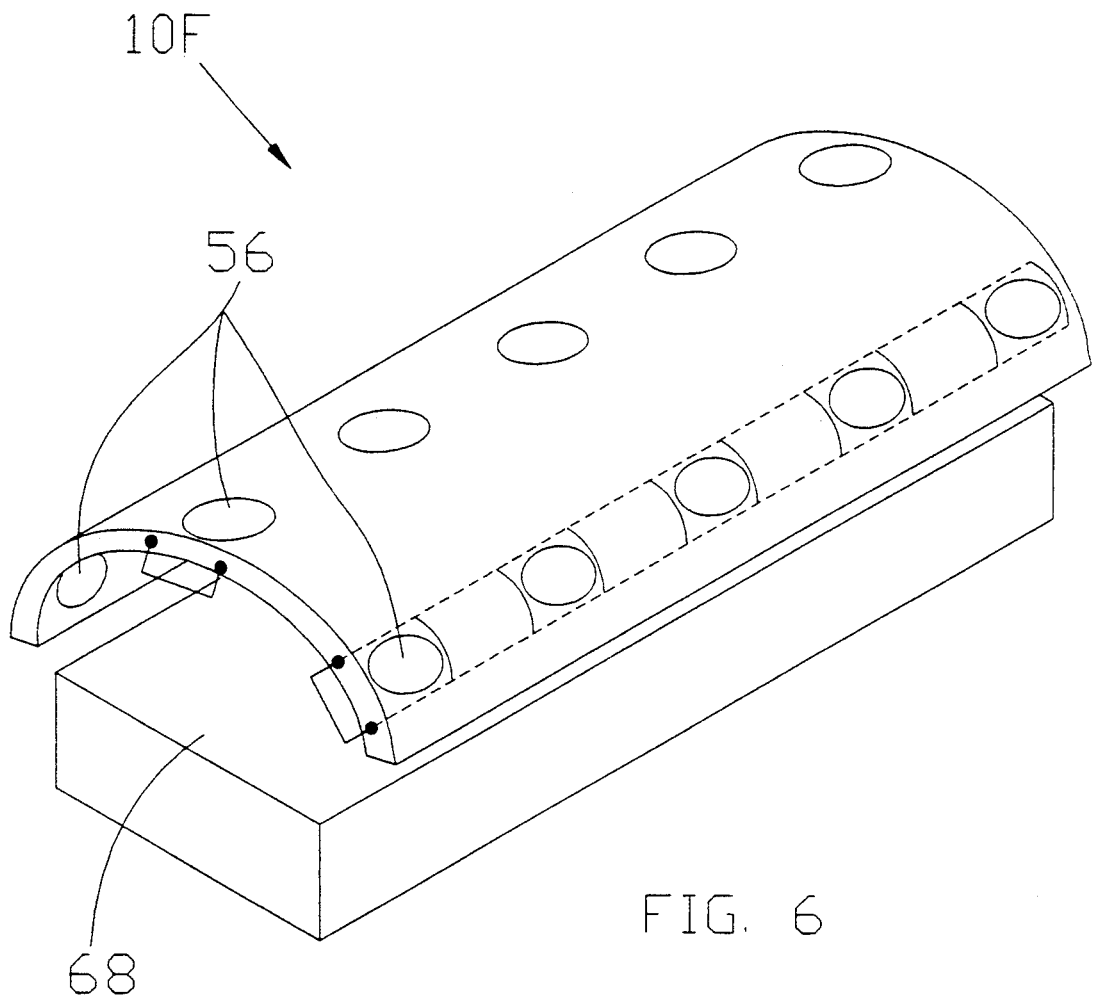
FIG. 6 shows the electronic embodiment of the present invention embodied within a conventional tanning booth.

Two basic embodiments of the present invention to generate discrete pulses are presented, mechanical generators shown in FIGS. 1, 2, 4, 5 and 7; and electronic pulse generators shown in FIGS. 4, 6 and 8.

Embodiment I: Mechanical Pulse Generation

Figure 1:
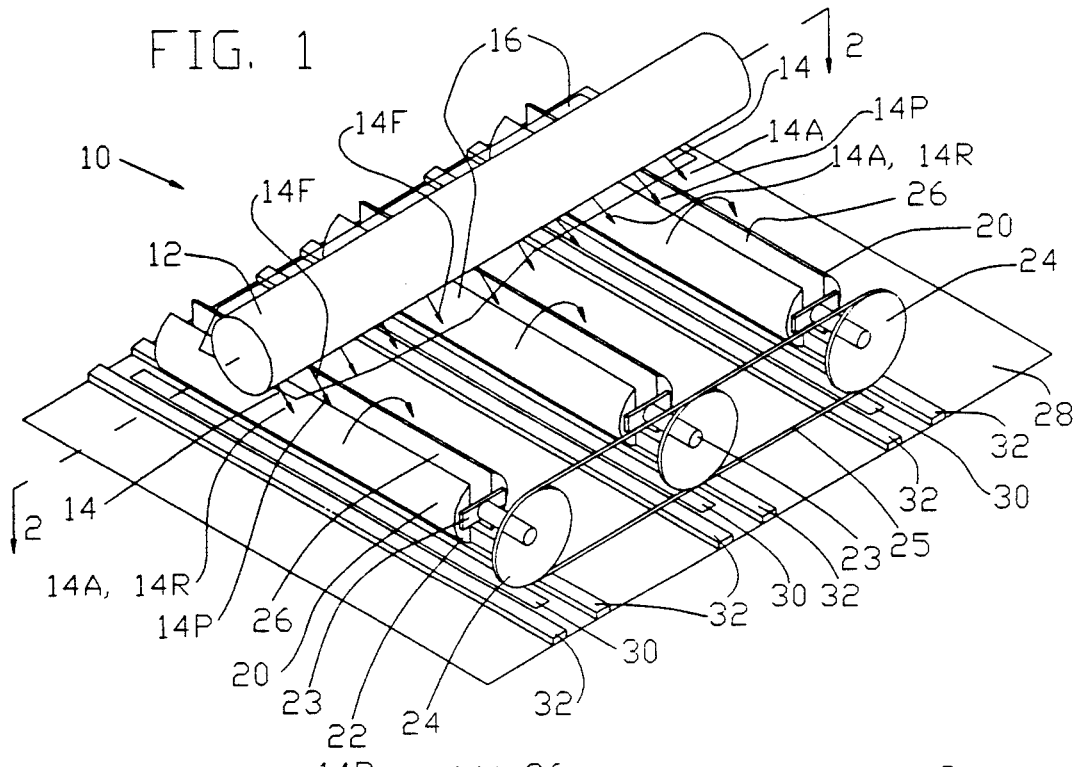
FIG. 1 depicts an apparatus to mechanically provide discrete pulses of light energy of selected wave length to effect tanning according to the present invention.
Figure 2:
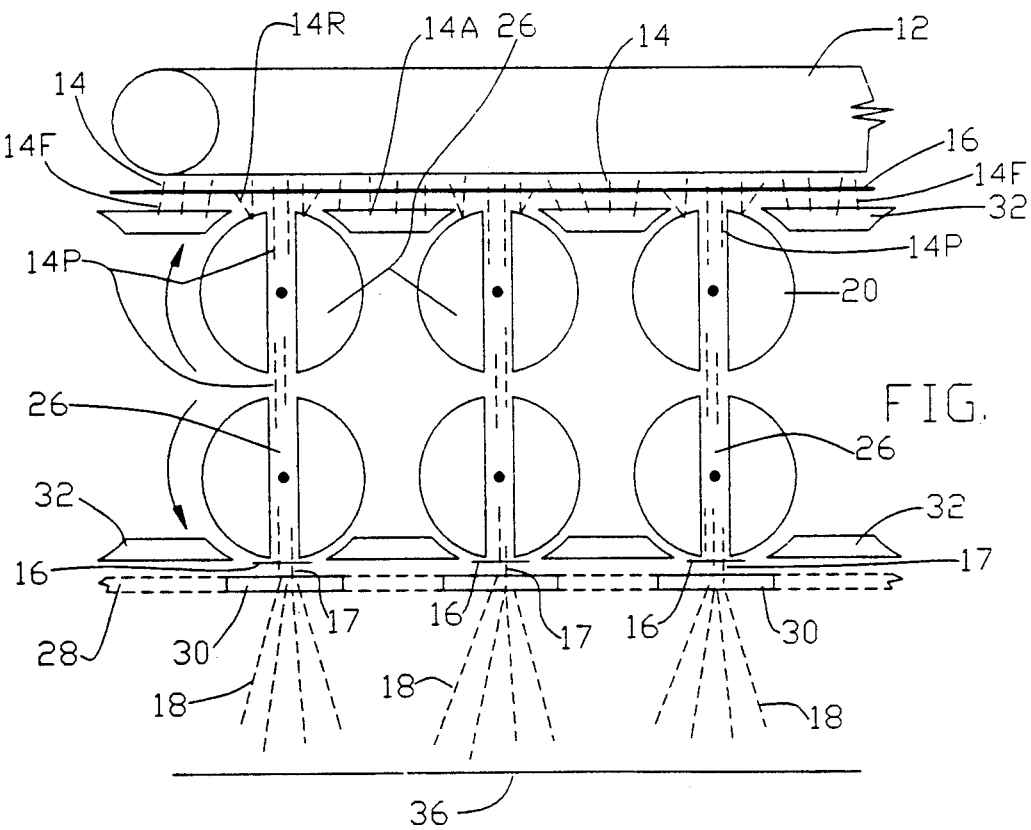
FIG. 2 is cross-section taken along line 2—2 of FIG. 1, showing more detail of a modified version of the device shown in FIG. 1.

Referring now to FIGS. 1 and 2, a mechanically-pulsed irradiation generation apparatus 10 is presented. A light source 12 is provided to generate light of first selected wave length 14 for tanning, within the range of 250 to 400 nm, preferably 280 to 300 nm and an apparent optimal wave length of about 290 nm. The preferred or optimum wave length of energy 14 may be selected by passing the energy through one or more transmittance filters 16, which may be made of UVT plastic 260 ($\frac{1}{4}$") available through EG&G Electro-Optics Division of EG&G, Inc., Salem Mass., or several other known materials, to produce filtered energy of selected wave length 14$f$.

In FIG. 1, unfiltered irradiation 14 is generated by light source 12 above path blocking means, in this case rapidly rotating cylinders 20. Cylinders 20 are connected at at least one of their longitudinal ends 22 by connecting means 23 to rotating means 24, in this case sprockets 24 driven by chain means 26. Sprockets 24 and chain means 26 are driven by any suitable power means (not shown). Cylinders 20 are fitted with a slit 26 extending therethrough and extending the length of cylinders 20. It is seen that only when slit 26 of cylinders 20 are in proper alignment is energy 14$p$ permitted to travel downward therethrough. When slits 26 are not in proper alignment, the path of filtered energy 14$f$ is periodically blocked because it is either reflected off 14$r$ or absorbed by 14$a$ cylinders 20.

It is further seen that much of the time the path of energy 14 is blocked. Irradiation is permitted to pass through slits 26 only for the brief discrete instant that slits 26 are in proper vertical alignment with light source 12. Otherwise, the path of energy is blocked by cylinders 20, and the energy is not passed into or emitted through slits 26. This results in discrete pulses of energy 17 being emitted from slits 26. A transmittance filter 16 may also be positioned at the exit end of slits 26, to provide discrete pulses of irradiation of selected wave length 18. Selected wave length irradiation 18 is then directed to the location 36 where the skin is to be effected. Preferably, when a plurality of cylinders is presented (to provide pulsed irradiation over a wider area, for example), chain means 25 is of the timing chain variety, so that sprockets 24 may be rotated rapidly in synchronization with each other sprocket, thereby presenting slits 26 in synchronized alignment to provide uniform pulsed energy over the area.

The mechanical pulse generation apparatus of FIG. 2 is provided with a filter block or grate 28 to prevent any light irradiation from passing therethrough and therebelow. Filter block 28 of FIG. 1 is provided with light energy passing means in the form of slots 30 aligned with slits 26 of rotating cylinders 20, and those slots 30 extend through the thickness of filter block 28 to permit the pulsed irradiation 17 to pass therethrough. To ensure that no unwanted light passes into slots 30, they are lined with blinders 32, made of any light absorbing material, such as closed cell foam or the like.

The mechanical pulse generation device of FIGS. 1 and 2 generates discrete pulses of selected energy having wave forms depicted in FIG. 7. When the slits 26 are not fully aligned with slots 30 and light source generator 12, the path of the irradiation is blocked and no irradiation is emitted, represented by the "zero" line of the various graphs. As shown in FIG. 7A, when slits 26, slots 30 and light source 12 are in alignment, positive energy of strength or power level "y" is emitted for a pulse duration of "x". When rotation of cylinders 20 drives slots 30, slits 26 and light source 12 out of alignment, the unit "goes dark" and no energy is emitted for a period of "z". The duration of each pulse and the dark time between pulses depends upon the geometry of cylinders 20 and slits 26. For example, when cylinders 20 are one inch in diameter and slits 26 are 0.165" wide, and they are rotated at 1000 revolutions per minute (rpm), the resulting discrete pulse of energy 17 emitted from the slots 30 of cylinder 20 is about 1.5 to 2.0 milliseconds.

Figure 7A:
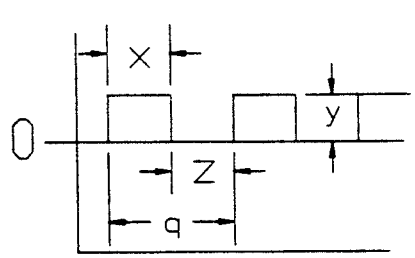
FIGS. 7A-7E depicts a representative wave form of discrete pulses generated by a mechanical pulse generator.
Figure 7B:
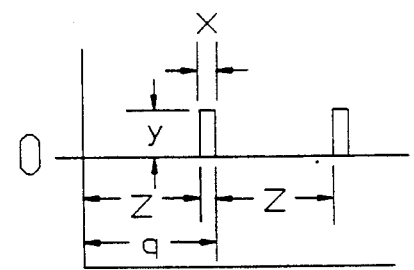
Figure 7C:
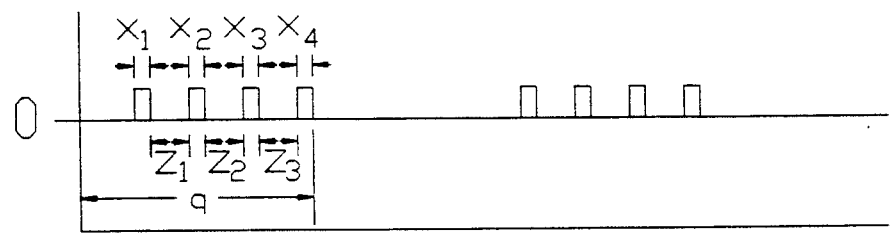
Figure 7D:
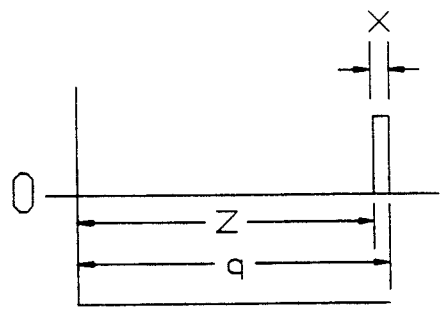
Figure 7E:
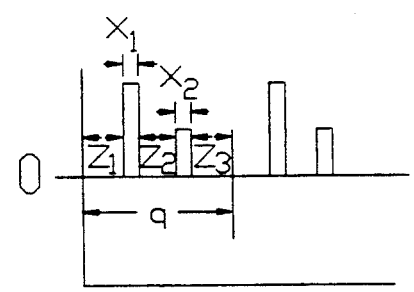

Different arrangements of cylinders 20, slots 30 and slits 26 would produce different pulse characteristics. For example, FIG. 7B shows two pulses of uniform duration and power, with a uniform dark time between each pulse. FIG. 7C shows a series of uniform relatively low power pulses separated by a dark time duration relatively the same length as the series of pulses. FIG. 7D shows a single pulse of higher power level after a relatively long dark period. FIG. 7E shows a repeating variable multiple pulse sequence, with a first higher power pulse followed by a short dark period and then a lower power burst of about the same pulse duration, followed by a longer dark period until the pulse cycle repeats. The variety of pulse patterns within a particular cycle is limited only by the geometric imagination of the designer. For example, FIG. 2 shows two rows of rotating cylinders 20, while FIG. 1 depicts a single array of cylinders 20. Similarly, transmittance filter(s) 16 can be interchanged so that a single device is capable of emitting discrete pulses of irradiation of two selected wave lengths.

Referring to FIGS. 4 and 5, alternate embodiments of mechanically-pulsed generation devices are presented. In FIG. 4, a pulse generator 10B is presented with a light source 12B for example, a series of fluorescent tubes emitting energy 14B of unfiltered or selected wave length. A transmittance filter 16B permits only selected wave length of energy 18B to pass therethrough. Light source 12B and filter 16B are positioned above a flat panel 36 which is rotated about rollers 38 which are powered (not shown) to rapidly rotate. Flat panel 36 is provided with a plurality of parallel slats 41 which are generally impervious to light and is further provided with a series of apertures 40, for example about 0.5" wide, through the thickness of panel 36.

As panel 36 is rotated about rollers 38 at about 1.5 feet per second, this causes upper slats 41 (and adjacent apertures 40) and lower slats 41 (and adjacent apertures 41) to contra-rotate with respect to each other. In this contra-rotating mode, the path of irradiation is blocked much of the time by the light-impervious slats 41; even when some irradiation is permitted through a top aperture 40, most of the time it will be blocked 40B by a bottom light-impervious slat 41. However, from time to time upper and lower apertures 40 will be placed in alignment as shown by 40A, which permits filtered light 17 to pass completely through rotating panel 36, thereby presenting discrete pulses of emitted energy of about 1.5 milliseconds duration. A further filter 42 may be provided to further modify the selected wave length of the emitted pulses of irradiation 44.

A device according to the embodiment depicted in FIG. 4 could be presented out of doors with the light source 12B being the sun. People could reside under device 10B and be subjected to only discrete pulses of energy from the sun, rather than being continuously exposed to the potentially damaging total array of UV energy normally presented by the sun. This could prevent skin damage in a major way.

In FIG. 5, an apparatus 10C is presented where the discrete pulses of energy are provided by directing light energy 14C from light sources 12C(1) and 12C(2) Without filtering (12C(1)) or through transmittance filters 16C (from 12C(2)), onto one or more rotating reflecting surfaces 42 (e.g., mirrors). Reflecting surfaces 42 are presented in triangular or other discrete polyhedral form, and rotated 43 about their axes 44. It is seen that reflecting surfaces 42 are only capable of reflecting for the discrete period of time that a planar surface 42p is presented, thereby generating discrete reflected pulses of light energy. This reflected irradiation may be further filtered by a transmittance filter 46, if further selection of optimum wave length is desired.

It will be apparent to those skilled in the art that the emitted wave form of the emitted pulses from the devices of FIGS. 4 and 5 will be similar to those wave forms depicted in FIG. 7. Again, a variety of pulse wave forms can be achieved, depending upon the geometric configuration(s) of the components.

Embodiment II: Stroboscopic Pulse Generation

Figure 3A:
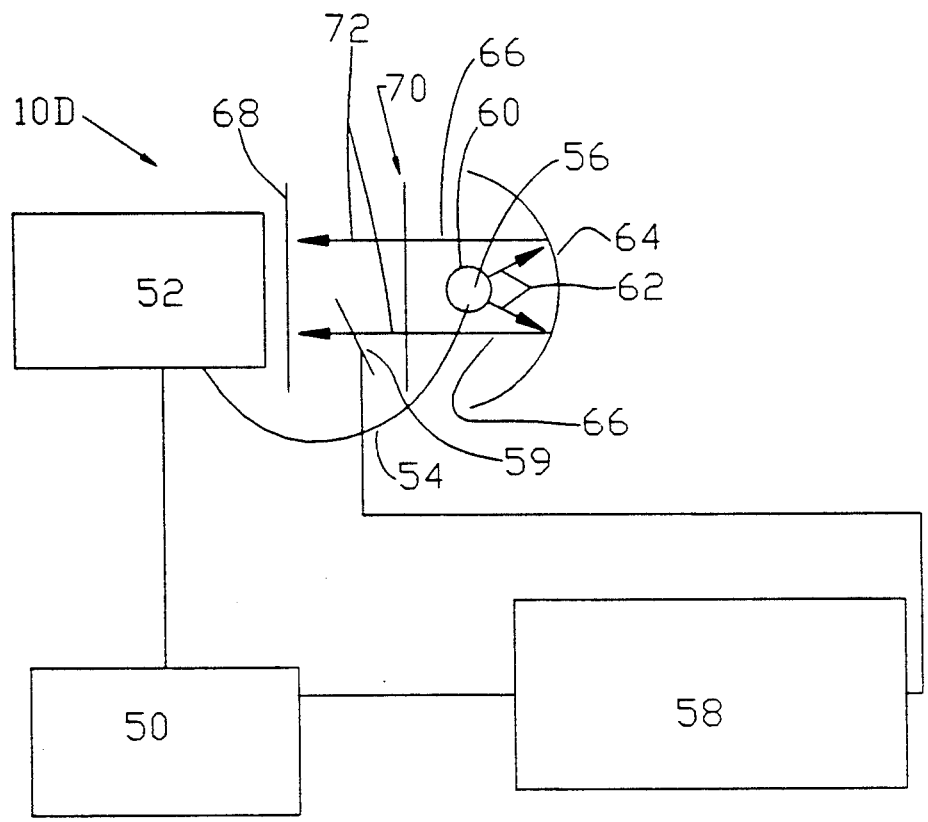
FIG. 3A is a schematic representation of a device to electronically produce discrete pulses of light energy of selected wave length.
Figure 3B:
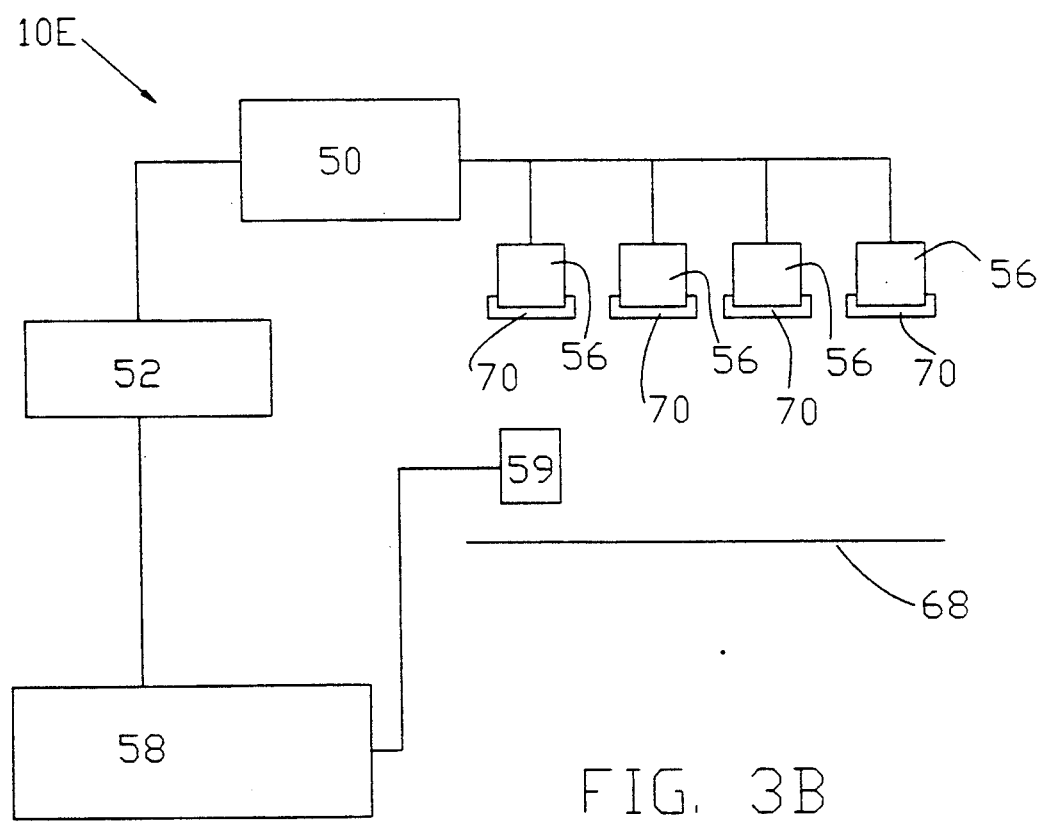
FIG. 3B shows the device of FIG. 3 with multiple electronic pulsed light generators to produce uniform pulsed irradiation over a wide area.

An electronic pulse generator 10D, utilizing stroboscopic flash tubes, is shown in FIGS. 3A and 3B. In FIG. 3A, the pulse generator 10D is presented with a power supply 50 linked to a lamp trigger to provide timed pulses or flashes of flashlamp 56 via connection 54. The duration and frequency of the pulses is controlled by a signal processing timing means 58 and signal detector means 59. Flashlamp devices (sometimes called flashtubes) are known for other unrelated applications and are available from, for example, EG&G Electro-Optics Division of EG&G, Inc. of Salem, Mass., EG&G has published several technical brochures and operating manuals for its flashlamps (e.g., Short-Arc Xenon Flashlamps and Power Supplies, Data Sheet F1022B-1 [3/88]; Flashlamp Applications Manual [4/88]), the disclosures of which are incorporated herein by reference. Continuous UV lamps for the mechanical pulse generators can be purchased from Southern New England Ultraviolet Co., Hamden, Conn., such as their model nos. RPR3500 (peak near 350 nm; 1/6 peak=320 nm; 4.5 watts) and RPR3000A (peak near 300 nm; 1/6 peak=270 nm; 15 watts).

In the device of FIG. 3A, by selecting the type of flashlamp 56 (e.g., a xenon flashlamp) and the glass envelope 60 surrounding flashlamp 56, the spectral output 62 of flashlamp 56 can be controlled to provide UV pulses of a selected wave length (e.g., a xenon flashtube will have an emission of UV irradiation of one general spectrum with most of the emission at a wave length of about 250–300 nm, while a krypton flashlamp will have a different spectral emission. In addition, the selection of the glass envelope 60 surrounding flashlamp 56 will also have an impact on the spectral emission of UV irradiation output 62. EG&G provides several different types of flashlamps and glass envelopes, which may be selected to achieve the desired spectral characteristics of UV output 62. For further details, see the aforementioned EG&G publications.

Pulsed flashlamp UV output 62 will typically (but not necessarily) be imposed upon a reflector surface 64, for example an aluminized reflector, which will reflect the UV pulses 66 toward the object to be irradiated 68. A transmittance filter 70 composed for example of UVT plastic may be interposed between reflector 64 and target location 68 to further filter the UV irradiation pulses to a more narrowly selected wave length. For example, an EG&G xenon strobe or flash lamp [with UV Glass Corning 9823] coupled with a 10 nm band width filter can selectively provide 285-295 nm light with pulse duration ranging from 10-100 microseconds. If desired, filter 70 can be placed closer in proximity to flashlamp 56, as shown in FIG. 3B.

I believe that maximum tanning in human skin will occur at a UV irradiation wave length of about 280 to 300 nm, preferably about 290 nm. By utilizing appropriate combinations of flashlamp 58 plus glass envelope 60 plus reflector surface 64 plus filter 70, the resulting filtered pulses of UV irradiation can be controlled to that selected wave length.

In apparatus 10E shown in FIG. 3B, it is seen that multiple flashlamps 56 can be arrayed to provide pulsed irradiation of selected frequency over a wider area. In FIG. 6, multiple flashlamps 56 are shown arrayed in a standard tanning booth 10F, which can irradiate a wide enough target location 68 with pulsed irradiation of selected wave length to promote tanning in an adult human.

Referring now to FIG. 8, it is seen that the wave form of pulses provided electronically or stroboscopically is different than the wave form of mechanically produced pulses (FIG. 7). Typically, within each energy cycle q, there is a rapid but not instantaneous energization toward a peak power or strength y, which only lasts for a short burst of time x. Then the pulse wave form rapidly decays towards a zero energy state. It is difficult to accurately portray the characteristics of an electronically produced pulse, because the time axis is so disproportionate. For example, in a total cycle time of q (say, one second) a typical xenon flashlamp available from EG&G will provide a total pulse duration of about 50 microseconds, leaving a dark portion of 999,950 microseconds; this ratio is impossible to show on a uniform time axis. Further, only a portion ("x") of that 50 microseconds will be at peak power ("y"), with the balance of the time utilized to bring the flashlamp rapidly up to peak ("p"), and then rapidly decaying to negligible ("d").

Figure 8A:
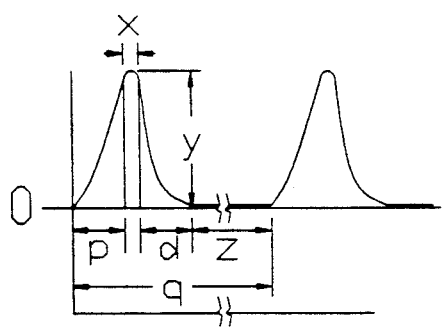
FIGS. 8A-8E depict representative wave forms of discrete pulses generated by an electronic pulse generator.
Figure 8B:
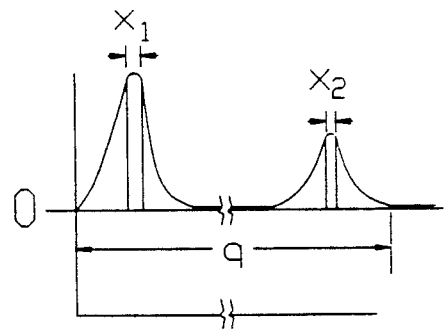
Figure 8C:
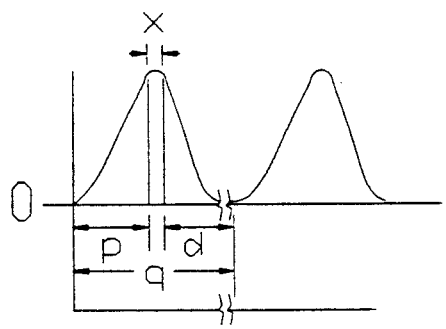
Figure 8D:
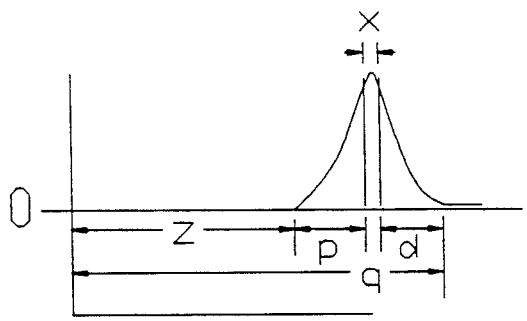
Figure 8E:
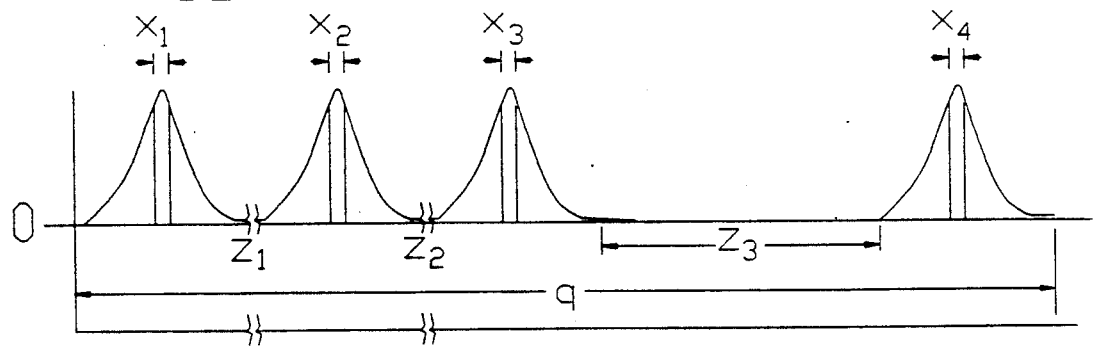

Referring to FIGS. 8B-8E, as with the mechanical pulse generator, a wide variety of electronically-generated cycle formats is available. FIG. 8B shows a cycle containing two pulses, with the first pulse being of greater power than the second. In FIG. 8C, a waveform with a longer time at peak is shown. In FIG. 8D, a single pulse preceded by a long dark period is shown. In FIG. 8E, a cycle is shown which contains three uniform bursts followed by a long dark period and concluding with a fourth pulse. The potential combinations of cycle formats and wave forms is virtually unlimited. Of course, the actual wave forms are quite variable, and reference should be had to the EG&G manual for more precise descriptions.

Referring again to FIGS. 7 and 8, the key to this invention is to provide, within each cycle ("q") of energy input, a "dark period" ("z") where negligible UV energy is impressed upon the skin. Energy exposure to the frequency selected for tanning-inducing irradiation (280-400 nm) is provided for only in very short, discrete pulses, which fill only a very short time portion ("x") of the total energy cycle (q=x+z), as shown in the various wave forms of FIGS. 7 and 8. For example, in a one-second energy cycle, an electronic embodiment of the present invention (e.g., the apparatus depicted and described in FIG. 3A/3B) would provide one pulse per second of energy of "y" power or strength for a duration "x", say 50 microseconds. For a pulse duration of 50 microseconds, the skin is exposed to energy for only 0.005% of the energy cycle; 99.995% of the energy cycle is "dark" time of negligible energy exposure.

A mechanical pulse generator as described above in FIG. 1 would produce a two millisecond pulse in each one second cycle, resulting in an energy cycle that would be 99.8% dark, and energized only 0.2% of the total cycle time. Electronic/stroboscopic pulse generators are available which could produce pulses in the range of 1 picosecond (0.000000001 sec) which could be of a very high power level to induce tanning with a single high power pulse, and leave the vast majority of the energy cycle as "dark" time (i.e., 99.9999999% dark). While the extreme proportions of the dark time may have greatest salutary effect on enhancing the cellular repairative process(es), it is expected that for some events, only a brief dark time will be sufficient to produce the desired result, say five to ten percent of the cycle time.

In FIG. 7C, a cycle containing four discrete pulses is shown. If the total cycle duration q is one second and each of these pulses is of 50 microseconds duration, the total energized portion of each one second cycle is 200 microseconds or 0.2 milliseconds. The total dark time associated with such a four-pulse cycle is therefore 99.98%; each cycle is only energized 0.02% of the time. Even when each pulse is a relatively long two milliseconds within a one second total cycle duration, the total energized portion of each cycle is only 0.2%; 99.8% of the cycle time is "dark" time. It is apparent that every embodiment of the present invention produces a total energy cycle wherein the vast majority of the total energy cycle time is "dark" time, thereby vastly reducing total cumulative energy exposure. Compared to continuous energization for the current state of the art tanning apparati, the present invention produces an energy cycle that is enormously less energy invasive, yet still produces the desired effect.

While the principles of this invention have been presented in illustrative embodiments, there are potentially many modifications of the light source (eximer lasers, for example, are capable of producing as many as 10,000 discrete pulses per second, each pulse having a duration on the order of picoseconds), mechanical modifications (belt technology for example), and gases used for the stroboscopic applications within the skill of the art which, if utilized, will be within the scope of this invention and the hereinafter appended claims.

I claim:

1. A method of tanning skin, said method comprising: exposing the skin to radiation energy from at least one radiation source for a plurality of pulse cycle periods, each of said plurality of pulse cycle periods having a total cycle time which includes a dark time during which the skin is exposed to negligible radiation energy, said dark time being more than one half of said total cycle time, said total cycle time for each of said plurality of pulse cycle periods having an equal time duration, each of said plurality of pulse cycle periods including at least one discrete pulse of radiation energy, wherein the at least one radiation source radiates energy selected from at least one wave length of between about 250 and 400 nanometers and wherein the skin is subjected to radiation energy for a selected number of pulse cycle periods per second.

2. A method as recited in claim 1, wherein the number of pulse cycle periods per second is selected from a range of from one (1) to 10,000 pulse cycle periods per second, and wherein said at least one discrete pulse of radiation energy within each pulse cycle period does not exceed five (5) discrete pulses.

3. A method as recited in claim 2, said at least one discrete pulse having a pulse duration time of from about 1 picosecond to about 20 milliseconds.

4. A method as recited in claim 1, wherein said at least one radiation source continuously radiates energy and wherein path blocking means creates said at least one discrete pulse of radiation energy during each of said plurality of pulse cycle period by periodically blocking the skin from exposure to said continuously radiated energy.

5. A method as recited in claim 1, wherein said at least one radiation source intermittently generates said at least one discrete pulse of radiation energy during each of said plurality of pulse cycle periods.

6. An apparatus for tanning skin, said apparatus comprising:
    means defining a location at which the skin is to be positioned for tanning; and,
    at least one electromagnetic pulse generating means for exposing the skin positioned for tanning to radiation energy for a plurality of pulse cycle periods, each of said plurality of pulse cycle periods having a total cycle time which includes a dark time during which the skin is exposed to negligible radiation energy, said dark time being more than one half of said total cycle time, said total cycle time for each of said plurality of pulse cycle periods having an equal time duration, each of said plurality of pulse cycle periods including at least one discrete pulse of electromagnetic radiation, wherein the at least one electromagnetic pulse generating means generates radiation selected from at least one wave length of between about 250 and 400 nanometers for a selected number of pulse cycle periods per second.

7. An apparatus as recited in claim 6, wherein each said discrete pulse has a pulse duration time of from about 1 picosecond to 20 milliseconds, the number of pulse cycle periods per second is selected from a range of from one (1) to 10,000 pulse cycle periods per second, and said at least one discrete pulse of electromagnetic radiation during each said pulse cycle does not exceed five (5) discrete pulses.

8. An apparatus as recited in claim 6, said at least one electromagnetic pulse generating means comprising:
    continuous electromagnetic generating means for continuously emitting electromagnetic radiation in a path towards said location defining means; and,
    path blocking means for periodically blocking the path of the continuously emitted electromagnetic radiation to obtain the discrete pulses of electromagnetic radiation.

9. An apparatus as recited in claim 8, said path blocking means comprising a plurality of parallel rotating slats located between said location defining means and said continuous electromagnetic generating means, each of the plurality of parallel rotating slats having an aperture therethrough to allow the passage of the continuously emitted electromagnetic radiation at a predetermined rotational position.

10. An apparatus as recited in claim 9, further comprising means for rotating said plurality of parallel rotatable slats at about 1.5 feet per second, and wherein said aperture of each of said plurality of rotating slats is approximately 0.5" in width, to produce a discrete pulse of electromagnetic irradiation of about 1.5 milliseconds.

11. An apparatus as recited in claim 8, said path blocking means comprising one or more rotatable cylinders located between said location defining means and said continuous electromagnetic generating means, each cylinder having an aperture therethrough to allow the passage of the continuously emitted electromagnetic radiation at a predetermined rotational position.

12. An apparatus as recited in claim 11, further comprising means for rotating said one or more cylinders at about 1000 revolutions per minute, and wherein said one or more cylinders has a diameter of about one inch and said aperture of each of said one or more cylinders has an opening width of approximately 0.165 inches.

13. An apparatus as recited in claim 8, said path blocking means comprising a plurality of parallel rotatable members and means for rotating said plurality of parallel rotatable members, each of the plurality of rotatable members having at least one reflective surface for, when said rotatable member is rotated, periodically reflecting the continuously emitted electromagnetic radiation towards said location defining means.

14. An apparatus for tanning skin, said apparatus comprising:
    means defining a location at which the skin is to be positioned for tanning; and
    at least one electromagnetic pulse generating means for exposing the skin positioned for tanning to radiation energy for a plurality of pulse cycle periods, each of said plurality of pulse cycle periods having a total cycle time which includes a dark time during which the skin is exposed to negligible radiation energy, said dark time being more than one half of said total cycle time, said total cycle time for each of said plurality of pulse cycle periods having an equal time duration, each of said plurality of electromagnetic radiation, said at least one discrete pulse of electromagnetic radiation, said at least one electromagnetic pulse generating means comprising at least one strobe light to intermittently produce electromagnetic irradiation.

15. An apparatus as recited in claim 14, wherein the intermittent electromagnetic radiation from said at least one strobe light is selected from at least one wave length of between about 250 and 400 nanometers for a selected number of pulse cycle periods per second.

16. An apparatus as recited in claim 15, wherein each said discrete pulse has a pulse duration time of from about 1 picosecond to 20 milliseconds, the number of pulse cycle periods per second is selected from a range of from one (1) to 10,000 pulse cycle periods per second, and said at least one discrete pulse of electromagnetic radiation during each said pulse cycle does not exceed five (5) discrete pulses.

17. An apparatus as recited in claim 15, said at least one electromagnetic pulse generating means further comprising a filter means, located between said at least one strobe light and said location defining means, for passing therethrough intermittent electromagnetic radiation of one or more selected wave length bands.

18. An apparatus as recited in claim 17 to induce tanning, wherein said selected wave length is about 290 nanometers.

19. An apparatus as recited in claim 14, said at least one strobe light being a xenon strobe lamp.

20. A method of tanning skin, said method comprising: exposing the skin to radiation energy from at least one radiation source for a plurality of pulse cycle periods, each of said plurality of pulse cycle periods having a total cycle time which includes a dark time during which the skin is exposed to negligible radiation energy, said dark time being more than one half of said total cycle time, said total cycle time for each of said plurality of pulse cycle periods having a time duration not exceeding one second, each of said plurality of pulse cycle periods including at least one discrete pulse of radiation energy.

21. A method as recited in claim 20, wherein the at least one radiation source radiates energy selected from at least one wave length of between about 250 and 400 nanometers.

22. A method as recited in claim 21, wherein the skin is subjected to radiation energy for a selected number of pulse cycle periods per second.

23. A method as recited in claim 22, wherein the number of pulse cycle periods per second is selected from a range of from one (1) to 10,000 pulse cycle periods per second, and wherein said at least one discrete pulse of radiation energy within each pulse cycle period does not exceed five (5) discrete pulses.

24. A method as recited in claim 23, said at least one discrete pulse having a pulse duration time of from about 1 picosecond to about 20 milliseconds.

25. A method as recited in claim 22, wherein said at least one radiation source continuously radiates energy and wherein path blocking means creates said at least one discrete pulse of radiation energy during each of said plurality of pulse cycle period by periodically blocking the skin from exposure to said continuously radiated energy.

26. A method as recited in claim 22, wherein said at least one radiation source intermittently generates said at least one discrete pulse of radiation energy during each of said plurality of pulse cycle periods.

27. An apparatus for tanning skin, said apparatus comprising:
means defining a location at which the skin is to be positioned for tanning; and,
at least one electromagnetic pulse generating means for exposing the skin positioned for tanning to radiation energy for a plurality of pulse cycle periods, each of said plurality of pulse cycle periods having a total cycle time which includes a dark time during which the skin is exposed to negligible radiation energy, said dark time being more than one half of said total cycle time, said total cycle time for each of said plurality of pulse cycle periods having a time duration not exceeding one second, each of said plurality of pulse cycle periods including at least one discrete pulse of electromagnetic radiation.

28. An apparatus as recited in claim 27, wherein the at least one electromagnetic pulse generating means generates radiation selected from at least one wave length of between about 250 and 400 nanometers for a selected number of pulse cycle periods per second.

29. An apparatus as recited in claim 28, wherein each said discrete pulse has a pulse direction time of from about 1 picosecond to 20 milliseconds, the number of pulse cycle periods per second is selected from a range of from one (1) to 10,000 pulse cycle periods per second, and said at least one discrete pulse of electromagnetic radiation during each said pulse cycle does not exceed five (5) discrete pulse.

30. An apparatus as recited in claim 28, said at least one electromagnetic pulse generating means comprising:
continuous electromagnetic generating means for continuously emitting electromagnetic radiation in a path towards said location defining means; and,
path blocking means for periodically blocking the path of the continuously emitted electromagnetic radiation to obtain the discrete pulses of electromagnetic radiation.

31. An apparatus as recited in claim 30, said path blocking means comprising a plurality of parallel rotating slats located between said location defining means and said continuous electromagnetic generating means, each of the plurality of parallel rotating slats having an aperture therethrough to allow the passage of the continuously emitted electromagnetic radiation at a predetermined rotational position.

32. An apparatus as recited in claim 31, further comprising means for rotating said plurality of parallel rotatable slats at about 1.5 feet per second, and wherein said aperture of each of said plurality of rotating slats is approximately 0.5" in width, to produce a discrete pulse of electromagnetic irradiation of about 1.5 milliseconds.

33. An apparatus as recited in claim 30, said path blocking means comprising one or more rotatable cylinders located between said location defining means and said continuous electromagnetic generating means, each cylinder having an aperture therethrough to allow the passage of the continuously emitted electromagnetic radiation at a predetermined rotational position.

34. An apparatus as recited in claim 33, further comprising means for rotating said one or more cylinders at about 1000 revolutions per minute, and wherein said one or more cylinders has a diameter of about one inch and said aperture of each of said one or more cylinders has an opening width of approximately 0.165 inches.

35. An apparatus as recited in claim 30, said path blocking means comprising a plurality of parallel rotatable members and means for rotating said plurality of parallel rotatable members, each of the plurality of rotatable members having at least one reflective surface for, when said rotatable member is rotated, periodically reflecting the continuously emitted electromagnetic radiation towards said location defining means.

36. An apparatus as recited in claim 27, said at least one electromagnetic pulse generating means comprising at least one strobe light to intermittently produce electromagnetic irradiation.

37. An apparatus as recited in claim 36, wherein the intermittent electromagnetic radiation from said at least one strobe light is selected from at least one wave length of between about 250 and 400 nanometers for a selected number of pulse cycle periods per second.

38. An apparatus as recited in claim 37, wherein each said discrete pulse has a pulse duration time of from about 1 picosecond to 20 milliseconds, the number of pulse cycle periods per second is selected from a range of from one (1) to 10,000 pulse cycle periods per second, and said at least one discrete pulse of electromagnetic radiation during each said pulse cycle does not exceed five (5) discrete pulses.

39. An apparatus as recited in claim 37, said at least one electromagnetic pulse generating means further comprising a filter means, located between said at least one strobe light and said location defining means, for passing therethrough intermittent electromagnetic radiation of one or more selected wave length bands.

40. An apparatus as recited in claim 39 to induce tanning, wherein said selected wave length is about 290 nanometers.

41. An apparatus as recited in claim 36, said at least one strobe light being a xenon strobe lamp.

* * * * *

UNITED STATES PATENT AND TRADEMARK OFFICE
CERTIFICATE OF CORRECTION

PATENT NO. : 5,282,842
DATED : Feb. 1, 1994
INVENTOR(S) : David G. Changaris

It is certified that error appears in the above-indentified patent and that said Letters Patent is hereby corrected as shown below:

Column 6, line 6, delete "With" insert --with--

Column 10, line 40, after "of" before "at" delete "electromagnetic radiation, said" insert --pulse cycle periods including--

Signed and Sealed this

Eighteenth Day of October, 1994

Attest:

BRUCE LEHMAN

Attesting Officer

Commissioner of Patents and Trademarks